United States Patent [19]

Grasser et al.

[11] Patent Number: 4,787,371

[45] Date of Patent: Nov. 29, 1988

[54] APPARATUS FOR THE DISINTEGRATION OF CALCULI

[75] Inventors: Franz Grasser, Eggolsheim; Manfred Rattner, Erlangen, both of Fed. Rep. of Germany

[73] Assignee: Siemens Aktiengesellschaft, Berlin & Munich, Fed. Rep. of Germany

[21] Appl. No.: 70,035

[22] Filed: Jul. 6, 1987

[30] Foreign Application Priority Data

Jul. 18, 1986 [DE] Fed. Rep. of Germany ....... 3624374

[51] Int. Cl.$^4$ ............................................. A61B 17/22
[52] U.S. Cl. .................... 128/24 A; 128/328
[58] Field of Search ...................... 128/660, 24 A, 328, 128/659

[56] References Cited

U.S. PATENT DOCUMENTS 4,609,940 9/1986 Born et al. .......................... 358/111

FOREIGN PATENT DOCUMENTS 0168559 4/1985 European Pat. Off. .
3122056 12/1982 Fed. Rep. of Germany .
3146628 6/1983 Fed. Rep. of Germany .
2002987 2/1979 United Kingdom .
2098425 11/1982 United Kingdom .

Primary Examiner—Ruth S. Smith
Attorney, Agent, or Firm—Hill, Van Santen, Steadman & Simpson

[57] ABSTRACT

An apparatus for disintegrating calculi situated in the body of a life form has a shock wave generator and an examination apparatus for locating the calculi within the body. The examination apparatus includes at least one image memory in which an image of a portion of the body, including the calculi to be disintegrated, is stored. A comparator compares the stored image with an image chronologically following the store image to determine any movement of the calculi which may have occurred between the generation of the compared images. The position of a shock wave generator relative to the calculi is set based on the stored image, and the shock wave generator is energized to disintegrate the calculi upon the recognition of a subsequent image most closely corresponding to the stored image.

9 Claims, 1 Drawing Sheet

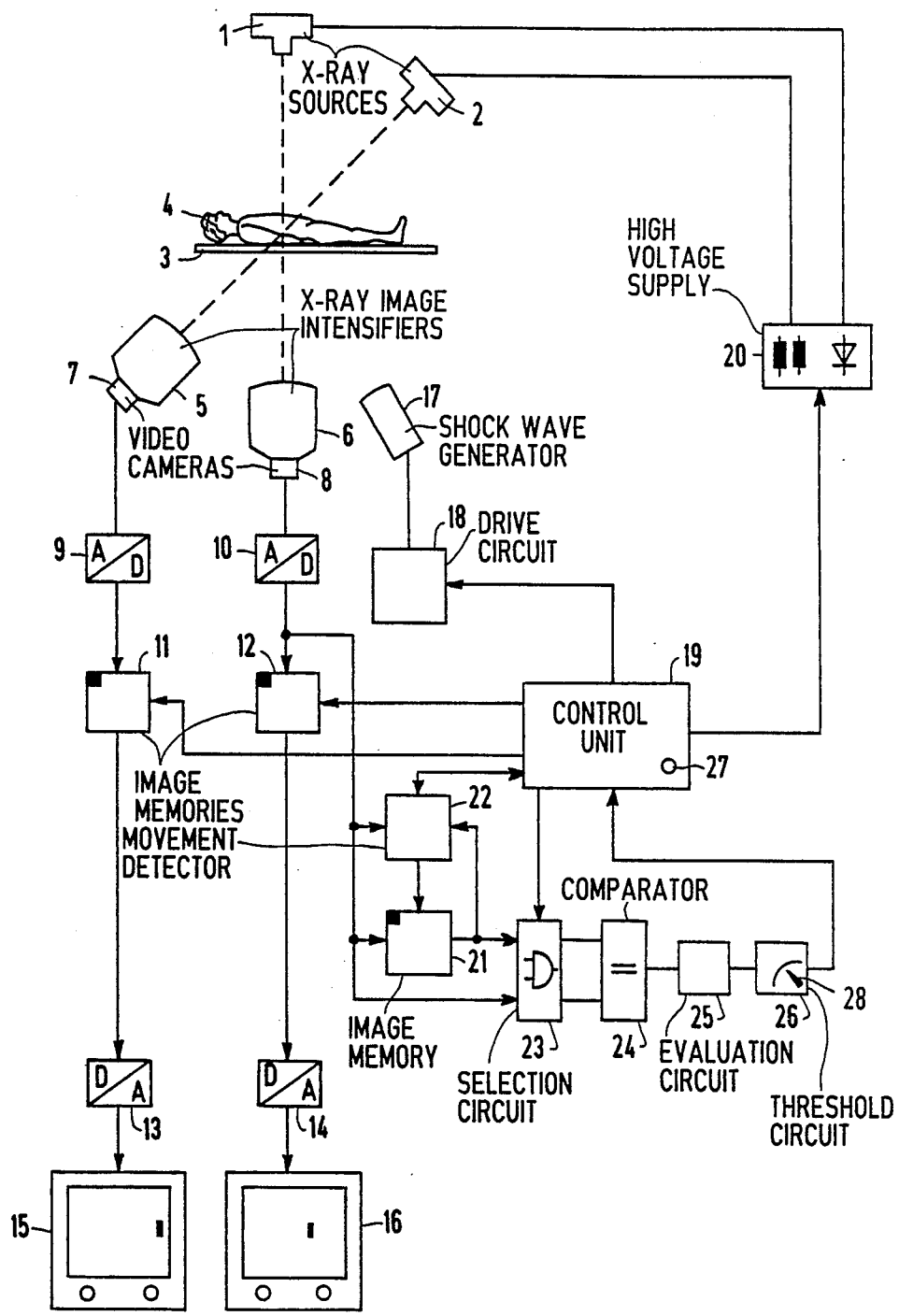

APPARATUS FOR THE DISINTEGRATION OF CALCULI

BACKGROUND OF THE INVENTION

1. Field of the Invention

The present invention is directed to an apparatus for disintegrating calculi situated in the body of a life form, and in particular to such an apparatus having a shock wave generator and an examination apparatus for locating the position of the calculi within the body for accurately positioning the shock wave generator.

2. Description of the Prior Art

An apparatus for disintegrating urinary and renal calculi, gallstones, or the like is disclosed in German OS No. 31 22 056. In this apparatus, a focussing chamber is used as a shock wave generator, in which a shock wave is generated by, for example, spark discharge. The shock wave is concentrated within the focussing chamber onto the calculus, and disintegrates the calculus. In order to make an exact determination as to whether the calculus is situated at the focal point of the focussing chamber, a locating apparatus is connected to an x-ray examination apparatus. In a transillumination mode, individual images of a stereo image pair are entered in an image memory in the video chain, being entered either individually or integrated over a plurality of images. A problem in accurately locating the position of such calculi arises, particularly when treating kidney stones, due to movement of such calculi during respiration. Thus the calculi may not be in the same position at the time the shock wave generator is energized to disintegrate the calculi as the calculi were at the time when the locating of the shock wave generator was initially set. The same problem can occur in the use of ultrasound examination devices.

SUMMARY OF THE INVENTION

It is an object of the present invention to provided an apparatus for disintegrating calculi making use of a shock wave generator and an apparatus for locating the calculi, wherein an extremely precise identification of the location of the calculi can be made at the point in time at which the shock waves are initiated, so that a reliable disintegration of the calculi is achieved, with minimum damage to healthy surrounding tissue.

The above object is achieved in accordance with the principles of the present invention in an apparatus for disintegrating calculi having an image memory in which an image containing the calculi is stored at the time the position of the shock wave generator is set relative to the calculi, and a comparison means for comparing the stored image with a chronologically following image. The comparison means determines when a chronologically following image most closely resembles the stored image, thus indicating, if movement has occurred due to, for example, respiration, between the images, the calculi has substantially returned to its initial position and the shock wave generator is then triggered. The shock waves can be triggered upon the occurrence of substantial equality the stored image with a current x-ray image or a current ultrasound image. Equality is only established, however, when the examination subject is at substantially the same position in a respiration cycle or a heartbeat cycle compared to the point in time at which the first image was stored. A precise coincidence of the localized point of the calculi with the focal point of the shock wave generator is thus achieved, so that the total energy expended can be utilized for comminuting the calculus and damage to healthy surrounding tissue is minimized.

Precise coincidence of the position of the calculi with the focal point of the shock wave generator can be even further improved by comparing images of only a small region of interest of the patient. This permits slight movements outside of the field of interest, and which would not significantly disturb the calculi disintegration, to be ignored. This can be accomplished, for example, by the use of an evaluation circuit which counts the number of equal or unequal picture elements in the compared images. Such an evaluation circuit may be connected to a threshold circuit which enables triggering of the shock waves only when the output of the evaluation circuit is above (if counting equal picture elements) or below (if counting unequal picture elements) a defined, adjustable threshold. Triggering of a plurality of shock waves in one motion phase is enabled by the use of a detector for a phase of minimal movement of the calculi, with the output signal of such a detector controlling the storing procedure of the image memory.

DESCRIPTION OF THE DRAWINGS

The single FIGURE is a schematic block diagram of an apparatus for disintegrating calculi in the body of a life form constructed in accordance with the principles of the present invention.

DESCRIPTION OF THE PREFERRED EMBODIMENTS

The apparatus constructed in accordance with the principles of the present invention shown in the drawing includes an x-ray examination apparatus having two x-ray sources 1 and 2 which generate respective x-ray beams in which an examination subject 4, having a calculus therein is disposed. The examination subject 4 is supported on a patient support 3. The x-ray attenuated by the examination subject 4 are incident on respective input luminescent screens of respective x-ray image intensifier 6 5 and 6. The x-ray source 1 and the x-ray image intensifier 6 may, for example, be arranged such that the central ray of the x-ray beam from the x-ray source 1 is perpendicular with respect to the examination subject 4 (a.p. projection). The x-ray source 2 and the x-ray image intensifier 5 may be obliquely arranged such that the central ray of the x-ray source 2 intersects the central ray of the x-ray source 1 at an angle of, for example, 45° at a target area inside the examination subject 4 (c.c. projection). As a result, transillumination images from two different projection directions are obtained, so that the examination subject 4 can be displaced using the patient support 3 so that the calculi are situated inthe target area of an apparatus for disintegrating the calculi, described below.

The output signals of video cameras 7 and 8 respectively coupled to the x-ray image intensifiers 5 and 6 are entered in two image memories 11 and 12 through respective analog-to-digital converters 9 and 10. The output signals from the image memories 11 and 12 can be viewed on respective monitors 15 and 16 through respective digital-to-analog converters 13 and 14. When the calculi are situated in the target area, the calculi appear in the center of the picture screens of the monitors 15 and 16.

A shock wave generator 17 is provided for comminuting the calculi situated in the target area. The shock wave generator is schematically shown in the drawing. The shock wave generator 17 generates shock waves in a known manner, resulting in disintegration of the calculi. Most effective results are obtained when the calculi are situated in the focal point of the shock wave generator 17. The examination apparatus and the shock wave generator 17 are permanently connected to each other such that the shock waves are focussed at the target area of the x-ray examination apparatus. The shock wave generator 17 is operated by a drive circuit 18. A control unit 19 is connected to a high voltage supply 20 for supplying the x-ray sources 1 and 2. The control unit 19 is also connected to the image memories 11 and 12, and to the drive circuit 18 for the shock wave generator 17.

The output signal of the analog-to-digital converter 10 is supplied to a further image memory 21, having a control input connected to the control unit 19 through a detector 22. The detector 22 detects miminal motion of the calculi resulting from patient movement, such as by respiration or heart activity. The detector 22 is also supplied with the current video signal from the analog-to-digital converter 10, and with the stored video signal from the image memory 21. The outputs of the image memory 21 and the analog-to-digital converter 10 are connected to a comparator 24 through a selection circuit 23. The output signal of the comparator 24 supplies a signal to the control unit through an evaluation circuit 25 and a threshold circuit 26.

At the beginning of an examination, the x-ray sources 1 and 2 are energized, so that x-ray images of the examination subject 4 are produced, and are entered in the image memories 11 and 12. The x-ray images are viewed on the monitors 15 and 16. By appropriately shifting the patient support 3, the examination subject 4 is aligned such that the calculi to be disintegrated are situated in the target area. This position of the examination subject 4 can be identified when the calculi are located in the center of the picture screens of the monitors 15 and 16. This alignment is undertaken in the transillumination mode.

After patient alignment has been completed, storage of an x-ray image into the further image memory 21 can be initiated, for example by actuation of a knob 27 on the control unit 19. The control unit 19 then enables the detector 22. The detector 22 enables entry of successive x-ray images, into the further image memory 21. By comparing the stored and current video signals, the phase having the least movement of the calculi is identified by, the detector 22, and the image entry procedure is terminated. The result is storage of an x-ray image corresponding to the phase of least movement of the calculi in the further image memory 21.

The detector 22 then provides an answerback signal to the control unit 19. The control unit 19 then drives the selection unit 23, enabling the selected picture elements corresponding to an area of interest to be transmitted to the comparator 24. Such selection can be undertaken in a known manner, for example, by a light cursor (not shown) on the monitor 16. It is also possible, because the calculi will always be situated in the center of the x-ray image displayed on the monitor 16, to transfer a predetermined prescribed central region of the image. It is also possible, instead of a selected area, to supply complete x-ray images to the comparator 24.

The comparator 24 compares the stored and the current video signals picture element-by-picture element, and generates an output signal corresponding to the number of identical and/or non-identical picture elements in those images. The comparator 24 may alternatively be a subtraction stage, which generates a difference signal for those picture elements which deviate from one another.

An evaluation circuit 25 is connected to the output of the comparator 24, and may consist, for example, of one or more adders which total the number of identical and/or non-identical picture elements. If the counter reading corresponding to the number of identical picture elements exceeds a threshold set by an adjustment means 28 of the threshold circuit 26, the threshold circuit 26 generates an enabling signal for the shock wave generator 17, supplied thereto through the control unit 19 and the drive circuit 18. The number of non-identical picture elements may also be evaluated, in which case the threshold circuit 26 generates an enabling signal when the output of the evaluation circuit 25 is below a threshold set by the adjustment means 28.

Shock waves are thus triggered only when the calculi in the examination subject 4 are disposed in their phase of least movement.

If the x-ray examination apparatus is to be operated only in the transillumination mode, the image memories 11 and 12 can be omitted. It is alternatively possible to omit only the image memory 12, if the output signal of the image memory 11 is supplied to both the digital-to-analog converters 13 and 14, and thus to both monitors 15 and 16. In a further embodiment, the calculi movement in various directions can be monitored by connecting the same circuit elements 21 through 28 to the output of the analog-to-digital converter 9, which supplies an image of the second x-ray projection.

Instead of coupling the video signal from the x-ray examination apparatus for use in triggering the shock waves, the trigger pulses may be acquired from the picture signal, of an ultrasound examination apparatus. The radiation dose applied to the patient is thus eliminated. It is also possible, instead of using a separate ultrasound examination apparatus, to use the mechanical energy of the shock wave reflected by the calculus for generating the image used for comparison. The costs for the overall installation can be thereby reduced.

Although modifications and changes may be suggested by those skilled in the art it is the intention of the inventors to embody within the patent warranted hereon all changes and modifications as reasonably and properly come within the scope of their contribution to the art.

We claim as our invention:

1. An apparatus for disintegrating calculi subject to movement in the body of an examination subject comprising:

triggerable means for directing shock waves at said calculi for the disintegration thereof;

means for generating a first image of a region of said examination subject in which said calculi are disposed;

said means for generating said first image subsequently generating a plurality of successive images of said region;

means for comparing said successive images with said first image for determining movement of said calculi in said successive images with respect to said first image; and means for triggering said means for directing shock waves to disintegrate said calculi when selected comparison criteria are met in said means for comparing indicating a smallest amount of movement of said calculi.

2. An apparatus as claimed in claim 1, further comprising means for selecting the size of said image of said region to which said criteria are applied.

3. An apparatus as claimed in claim 1, wherein each of said first image and said successive images consist of a plurality of picture elements, wherein said means for comparing compares the number of non-identical picture elements in said first image and in said successive images and generates an output signal corresponding to said number, and further comprising a threshold circuit to which said output signal from said means for comparing is supplied, said threshold circuit generating a trigger signal for said means for directing shock waves when said output signal of said means for comparing is below a selected threshold level.

4. An apparatus as claimed in claim 1, wherein each of said first image and said successive images consist of a plurality of picture elements, wherein said means for comparing compares the number of identical picture elements in said first image and in said successive images and generates an output signal corresponding to said number, and further comprising a threshold circuit to which the output signal of said means for comparing is supplied, said threshold circuit generating a trigger signal for said means for directing shock waves when said output signal is above a selected threshold level.

5. An apparatus as claimed in claim 1, further comprising:
  means for detecting an image of said region of said examination subject in which a phase of minimal movement of said calculi is present; and
  means for storing said image having said phase of minimal movement for use as said first image.

6. An apparatus as claimed in claim 1, wherein said means for generating said first image and said plurality of successive images is an x-ray examination system.

7. An apparatus as claimed in claim 1, further comprising means for positioning said means for directing shock waves relative to said calculi using said first image.

8. An apparatus for disintegrating calculi subject to movement in the body of an examination subject comprising:
  means for generating a plurality of successive images of a region of said examination subject in which said calculi are disposed;
  triggerable means for directing shock waves at said calculi for disintegration thereof;
  means for detecting one of said images in which said calculi exhibit a phase of minimal movement;
  means for storing said one of said images;
  means for comparing a remainder of said successive images to said one of said images; and
  means for triggering said means for directing shock waves based on a result of the comparison in said means for comparing.

9. An apparatus as claimed in claim 8, further comprising means for selecting criteria for said comparison.

* * * * *